United States Patent
Jessop et al.

(10) Patent No.: US 9,220,577 B2
(45) Date of Patent: *Dec. 29, 2015

(54) SYRINGE-TO-SYRINGE MIXING SYSTEMS AND RELATED APPARATUS AND METHODS

(71) Applicant: Ultradent Products, Inc., South Jordan, UT (US)

(72) Inventors: Neil T. Jessop, Sandy, UT (US); Bruce S. McLean, Sandy, UT (US); Jared Sheetz, Eagle Mountain, UT (US)

(73) Assignee: Ultradent Products, Inc., South Jordan, UT (US)

( * ) Notice: Subject to any disclaimer, the term of this patent is extended or adjusted under 35 U.S.C. 154(b) by 149 days.

This patent is subject to a terminal disclaimer.

(21) Appl. No.: 13/741,952

(22) Filed: Jan. 15, 2013

(65) Prior Publication Data

US 2013/0130197 A1  May 23, 2013

Related U.S. Application Data

(63) Continuation of application No. 12/525,961, filed as application No. PCT/US2007/067556 on Apr. 26, 2007, now Pat. No. 8,454,558, which is a continuation of application No. 11/673,334, filed on Feb. 9, 2007, now Pat. No. 7,776,010.

(51) Int. Cl.
  *A61M 5/19* (2006.01)
  *A61C 5/04* (2006.01)
  (Continued)

(52) U.S. Cl.
  CPC . *A61C 5/04* (2013.01); *A61C 5/062* (2013.01); *A61M 5/2448* (2013.01);
  (Continued)

(58) Field of Classification Search
  CPC ............... A61M 5/31596; A61M 2005/31598; A61M 5/31511; A61M 5/284; A61C 5/04; A61C 5/062
  USPC .................... 604/82, 87, 89, 90, 91
  See application file for complete search history.

(56) References Cited

U.S. PATENT DOCUMENTS

| 2,798,488 A | 7/1957 | Hall |
| 2,869,543 A | 1/1959 | Ratcliff et al. |

(Continued)

FOREIGN PATENT DOCUMENTS

| AU | 2007347133 | 8/2008 |
| EP | 1479364 | 5/2004 |

(Continued)

OTHER PUBLICATIONS

U.S. Appl. No. 61/024,379, filed Jan. 29, 2008, Kennard.
(Continued)

*Primary Examiner* — Aarti B Berdichevsky
(74) *Attorney, Agent, or Firm* — Workman Nydegger

(57) ABSTRACT

A hollow syringe barrel for use in syringe mixing systems for mixing a two-component composition. A hollow body of the syringe barrel includes a proximal end, a distal end, and continuous cylindrical wall defining an internal chamber for containing a first component. A rupturable membrane disposed at the distal end caps and seals off a single dispensing orifice. A second syringe barrel can be coupled to the distal end of the hollow syringe barrel to form a syringe-to-syringe mixing system. First and second plungers disposed within the hollow syringe barrel and second syringe barrel, respectively, are used to mix and cycle back and forth first and second components initially contained within the hollow syringe barrel and second syringe barrel. The two components are initially separated by the rupturable membrane, which is irreversibly ruptured by applying sufficient pressure to the first plunger within the hollow syringe barrel prior to mixing.

28 Claims, 7 Drawing Sheets

(51) Int. Cl.

| | | |
|---|---|---|
| A61M 5/315 | (2006.01) | |
| A61M 5/24 | (2006.01) | |
| A61C 5/06 | (2006.01) | |
| B65D 25/08 | (2006.01) | |
| B65D 77/04 | (2006.01) | |
| B65D 83/00 | (2006.01) | |
| B65B 3/00 | (2006.01) | |

(52) U.S. Cl.
CPC ............ *A61M 5/31596* (2013.01); *B65B 3/006* (2013.01); *B65D 25/082* (2013.01); *B65D 77/0486* (2013.01); *B65D 83/0005* (2013.01); *Y10T 29/49826* (2015.01)

(56) References Cited

U.S. PATENT DOCUMENTS

| | | |
|---|---|---|
| 3,281,124 A | 10/1966 | Pawlowski et al. |
| 3,326,215 A | 6/1967 | Sarnoff et al. |
| 3,348,546 A | 10/1967 | Roberts et al. |
| 3,548,825 A | 12/1970 | Shaw |
| 3,663,501 A | 5/1972 | Adams et al. |
| 3,685,514 A | 8/1972 | Cheney |
| 3,724,076 A | 4/1973 | Schmitz |
| 3,749,084 A | 7/1973 | Cucchiara |
| 3,756,390 A | 9/1973 | Abbey et al. |
| 3,767,085 A | 10/1973 | Cannon et al. |
| 3,831,316 A | 8/1974 | Pauliukonis |
| 3,872,864 A | 3/1975 | Allen, Jr. |
| 3,940,362 A | 2/1976 | Overhults |
| 4,003,709 A | 1/1977 | Eaton et al. |
| 4,083,955 A | 4/1978 | Grabenstetter et al. |
| 4,150,012 A | 4/1979 | Joos |
| 4,159,570 A | 7/1979 | Baskas et al. |
| 4,215,985 A | 8/1980 | Madlener |
| 4,229,813 A | 10/1980 | Lilly et al. |
| 4,235,633 A | 11/1980 | Tomioka et al. |
| 4,243,080 A | 1/1981 | Choksi et al. |
| 4,292,916 A | 10/1981 | Bradley et al. |
| 4,313,440 A | 2/1982 | Ashley |
| 4,331,146 A | 5/1982 | Brignola |
| 4,374,937 A | 2/1983 | Nemcek et al. |
| 4,391,798 A | 7/1983 | Tavss et al. |
| 4,412,836 A | 11/1983 | Brignola |
| 4,463,875 A | 8/1984 | Tepic |
| 4,464,174 A | 8/1984 | Ennis |
| 4,476,866 A | 10/1984 | Chin |
| 4,480,760 A | 11/1984 | Schonberger |
| 4,515,586 A | 5/1985 | Mendenhall et al. |
| 4,657,941 A | 4/1987 | Blackwell et al. |
| 4,693,706 A | 9/1987 | Ennis, III |
| 4,743,229 A | 5/1988 | Chu |
| 4,776,704 A | 10/1988 | Kopunek et al. |
| 4,966,468 A | 10/1990 | Bruning |
| 4,987,849 A | 1/1991 | Sherman |
| 5,000,939 A | 3/1991 | Dring et al. |
| 5,032,178 A | 7/1991 | Cornell |
| 5,045,283 A | 9/1991 | Patel |
| 5,053,339 A | 10/1991 | Patel |
| 5,057,434 A | 10/1991 | Prusik et al. |
| 5,228,573 A | 7/1993 | Pavelle et al. |
| 5,317,987 A | 6/1994 | Muller et al. |
| 5,328,462 A | 7/1994 | Fischer |
| 5,354,285 A | 10/1994 | Mazurik et al. |
| 5,367,002 A | 11/1994 | Huang et al. |
| 5,380,315 A | 1/1995 | Isono et al. |
| 5,395,241 A | 3/1995 | Kandelman |
| 5,395,325 A | 3/1995 | Moreno et al. |
| 5,425,580 A | 6/1995 | Beller |
| 5,429,603 A | 7/1995 | Morris |
| 5,489,267 A | 2/1996 | Moreno et al. |
| 5,509,530 A | 4/1996 | Wilson |
| 5,534,562 A | 7/1996 | Jensen et al. |
| 5,551,778 A | 9/1996 | Hauke et al. |
| 5,633,836 A | 5/1997 | Langer et al. |
| 5,643,206 A | 7/1997 | Fischer |
| 5,665,066 A | 9/1997 | Fischer |
| 5,697,903 A | 12/1997 | Fischer |
| 5,725,499 A | 3/1998 | Silverstein et al. |
| 5,743,886 A | 4/1998 | Lynn et al. |
| 5,756,356 A | 5/1998 | Yanagi et al. |
| 5,767,170 A | 6/1998 | Ibsen et al. |
| 5,779,668 A | 7/1998 | Grabenkort |
| 5,802,015 A | 9/1998 | Rothschild et al. |
| 5,839,592 A | 11/1998 | Hayes |
| 5,876,372 A | 3/1999 | Grabenkort et al. |
| 5,908,054 A | 6/1999 | Safabash et al. |
| 5,932,627 A | 8/1999 | Blackwell |
| 5,957,166 A | 9/1999 | Safabash |
| 5,981,620 A | 11/1999 | Hammesfahr et al. |
| 6,071,528 A | 6/2000 | Jensen et al. |
| 6,089,180 A | 7/2000 | Nichols, Jr. |
| 6,234,190 B1 | 5/2001 | Fischer et al. |
| 6,234,196 B1 | 5/2001 | Fischer et al. |
| 6,309,372 B1 | 10/2001 | Fischer et al. |
| 6,331,076 B1 | 12/2001 | Coll |
| 6,458,868 B1 | 10/2002 | Okada et al. |
| 6,500,879 B1 | 12/2002 | Huang et al. |
| 6,501,390 B1 | 12/2002 | Chainer et al. |
| 6,524,559 B2 | 2/2003 | Urai et al. |
| 6,527,751 B2 | 3/2003 | Fischer et al. |
| 6,540,072 B1 | 4/2003 | Fischer |
| 6,575,930 B1 | 6/2003 | Trombley, III et al. |
| 6,592,251 B2 | 7/2003 | Edwards et al. |
| 6,612,465 B2 | 9/2003 | Pierson et al. |
| 6,685,923 B2 | 2/2004 | Peterson et al. |
| 6,715,645 B2 | 4/2004 | Peuker et al. |
| 6,743,194 B2 | 6/2004 | Sharon et al. |
| 6,756,417 B2 | 6/2004 | Allred et al. |
| 6,759,449 B2 | 7/2004 | Kimura et al. |
| 6,817,987 B2 | 11/2004 | Vetter et al. |
| 6,818,682 B2 | 11/2004 | Falsafi et al. |
| 6,846,300 B2 | 1/2005 | Horth et al. |
| 6,884,071 B2 | 4/2005 | Martin |
| 6,921,380 B1 | 7/2005 | Epstein et al. |
| 7,166,651 B2 | 1/2007 | Qian |
| 7,168,847 B2 | 1/2007 | Frei et al. |
| 7,214,726 B2 | 5/2007 | Qian |
| 7,335,691 B2 | 2/2008 | Orlowski |
| 7,569,185 B2 | 8/2009 | Fischer |
| 7,776,010 B2 | 8/2010 | Jessop |
| 7,879,002 B2 | 2/2011 | Jessop |
| 8,394,052 B2 * | 3/2013 | Jessop et al. .................... 604/87 |
| 2001/0009931 A1 | 7/2001 | Pflug et al. |
| 2001/0016703 A1 | 8/2001 | Wironen et al. |
| 2001/0037091 A1 | 11/2001 | Wironen et al. |
| 2002/0072714 A1 | 6/2002 | Epstein et al. |
| 2003/0055685 A1 | 3/2003 | Cobb et al. |
| 2003/0186196 A1 | 10/2003 | Wang et al. |
| 2004/0054327 A1 | 3/2004 | Gillespie, III |
| 2004/0071638 A1 | 4/2004 | Simonton et al. |
| 2004/0122359 A1 | 6/2004 | Wenz et al. |
| 2004/0136924 A1 | 7/2004 | Boyd et al. |
| 2005/0014861 A1 | 1/2005 | Qian |
| 2005/0023173 A1 | 2/2005 | Paoletti |
| 2005/0105385 A1 | 5/2005 | McGill et al. |
| 2005/0177100 A1 | 8/2005 | Harper et al. |
| 2005/0281759 A1 | 12/2005 | Tung |
| 2006/0004120 A1 | 1/2006 | Orlowski et al. |
| 2006/0171903 A1 | 8/2006 | Yamagishi et al. |
| 2007/0003493 A1 | 1/2007 | Simonton et al. |
| 2007/0088097 A1 | 4/2007 | Qian |
| 2007/0092451 A1 | 4/2007 | Loveridge |
| 2007/0099156 A1 * | 5/2007 | Wagner et al. .............. 433/228.1 |
| 2007/0106210 A1 * | 5/2007 | Fischer .......................... 604/82 |
| 2007/0183986 A1 | 8/2007 | Wagner |
| 2007/0203257 A1 | 8/2007 | Qian |
| 2007/0251839 A1 * | 11/2007 | Jessop et al. ................... 206/221 |
| 2007/0255200 A1 | 11/2007 | McLean |
| 2007/0255201 A1 | 11/2007 | McLean |
| 2007/0255204 A1 | 11/2007 | McLean |
| 2009/0024082 A1 | 1/2009 | McLean |
| 2009/0191279 A1 | 7/2009 | Kennard |

(56) References Cited

U.S. PATENT DOCUMENTS

| | | | |
|---|---|---|---|
| 2010/0221678 A1 | 9/2010 | Fischer | |
| 2010/0307935 A1 | 12/2010 | Jessop | |
| 2010/0323322 A1 | 12/2010 | Jessop | |

FOREIGN PATENT DOCUMENTS

| | | |
|---|---|---|
| FR | WO9926581 | 6/1999 |
| FR | WO2005016170 | 2/2005 |
| JP | 50049358 | 5/1975 |
| JP | 1315327 | 12/1989 |
| JP | 05320032 | 12/1993 |
| JP | 9182760 | 7/1997 |
| JP | 2005-104534 | 4/2005 |
| JP | 5104531 | 4/2005 |
| JP | 2005-186026 | 7/2005 |
| MX | MX/a/2009/008519 | 8/2007 |
| WO | WO9209870 | 6/1992 |
| WO | 9965597 | 12/1999 |
| WO | WO2005050192 | 6/2005 |
| ZA | 9403163 | 1/1995 |

OTHER PUBLICATIONS

U.S. Appl. No. 61/049,643, filed May 1, 2008, Kennard.

"52-11 SureFil High Density Posterior Restorative (project 98-56)", General Dentistry, pp. 1-9, http://www.brooks.af.mil/dis/DIS58/sec5a.htm (Jun. 2, 2005).

"Information for Health Professionals Data Sheet", Atridox, http://www.medsafe.govt.nz/Profs/Datasheet/a/Atridoxgel.htm, Jun. 3, 2005 (7 pages).

Seppa, L., et al., "Caries-preventive effect of fluoride varnish with different fluoride concentrations," Caries Research, vol. 28(1), pp. 64/67 (Feb. 3, 1993).

Kozykowsky, V., et al., "Histological study of the effect of fluoride preparations for topical use on in vitro treated human enamel surfaces," Deutsche Stematologie, vol. 23(11), pp. 809-816 (Nov. 1973).

Merck Index, online edition, accessed Sep. 15, 2008, NaF.

He et al., "Monolayer formation of Alkyl Chain-Containing Phosphoric Acid Amphiphilies at the Air/Water (pH 5.6) Interface: Influence of Temperature and Cations", Journal of Colloidal and Interface science 246, 335-342 (Feb. 15, 2002).

Shen et al,. "Assessing fluoride concentration uniformity and fluoride release from three varnishes", American Dental Association, vol. 133, Feb. 2002 (Abstract).

Williams, B., et al., "Fissure sealants: a 4-year clinical trial comparing an experimental glass polyalkenoate cement with a bis glycidyl metharcylate resin used as fissure sealants," Br dent J. Feb. 10, 1996;180(3):104-8 Accession No. 8746143 [PubMed—Indexed for MEDLINE] (Abstract).

Ripa, L., Sealants Revisited: an update of the effectiveness of pir-and-fissure sealants, Caries Res. Dec. 1993;27 Suppl 1:77-82 Accession No. 8500131 [PubMed—Indexed for MEDLINE](abstract).

Irmansyah et al., "In vitro fluoride uptake by bovine enamel during use of cyanoacrylate adhesives containing fluoride compounds," Journal of Materials Science: Materials in Medicine (Jul. 1990), 1(2), 110-13 Accession No. 1990:618156 CAPLUS (Abstract).

Irmansyah et al., "A caries prophylactic study on artificial lesions in bovine tooth enamel coated with cyanoacrylate adhesives containing fluoride compounds," Journal of Materials Science: Materials in Medicine (Jul. 1990), 1(2), 118-22 Accession No. 1990:618158 CAPLUS (Abstract).

Wakasa, K., "Dental use of alkyl cyanoacrylate monomer including fluoride compounds as a coating agent," Journal of Materials Science Letters (Jan. 1992), 11(5), 286-7 Accession No. 1992:158871 CAPLUS (Abstract).

Boyanov, B., et al., "Study of the effect of fluoride on the insulation properties of some alkyl-2-cyanoacrylate preparations for caries-prevention," Problemi na Stomatologiyata (1976) Moscow, 4, 9-15 Accession No. 1978:83415 CAPLUS (Abstract).

Swartz, et al., "Addition of Fluoride to Pit and Fissure Sealants—A Feasability Study," J. Dent. Res., vol. 55, No. 5, pp. 757-771 (Sep. 1976) (Abstract).

U.S. Appl. No. 11/348,055, filed Apr. 30, 2008, Office Action.
U.S. Appl. No. 11/537,807, filed Jun. 23, 2008, Office Action.
U.S. Appl. No. 11/673,334, filed Aug. 29, 2008, Office Action.
U.S. Appl. No. 11/348,055, filed Sep. 17, 2008, Office Action.
U.S. Appl. No. 11/537,807, filed Dec. 17, 2008, Office Action.
U.S. Appl. No. 11/673,334, filed Jan. 21, 2009, Office Action.
U.S. Appl. No. 11/348,055, filed Apr. 2, 2009, Office Action.
U.S. Appl. No. 11/537,807, filed Apr. 17, 2009, Notice of Allowance.
U.S. Appl. No. 11/348,055, filed Aug. 31, 2009, Office Action.
U.S. Appl. No. 11/673,334, filed Sep. 29, 2009, Office Action.
U.S. Appl. No. 11/348,055, filed Feb. 4, 2010, Office Action.
U.S. Appl. No. 11/673,334, filed Mar. 9, 2010, Office Action.
U.S. Appl. No. 11/673,334, filed Jun. 2, 2010, Notice of Allowance.
U.S. Appl. No. 12/242,555, filed Nov. 22, 2010, Office Action.
U.S. Appl. No. 12/535,500, filed Nov. 24, 2010, Office Action.
U.S. Appl. No. 12/857,142, filed Mar. 4, 2011, Office Action.
U.S. Appl. No. 12/525,961, filed Mar. 9, 2011, Office Action.
U.S. Appl. No. 12/857,142, filed Aug. 11, 2011, Office Action.
U.S. Appl. No. 12/525,961, filed Sep. 1, 2011, Office Action.
U.S. Appl. No. 12/339,382, filed Aug. 17, 2012, Office Action.
U.S. Appl. No. 12/857,142, filed Sep. 26, 2012, Office Action.
U.S. Appl. No. 12/525,961, filed Sep. 27, 2012, Office Action.
U.S. Appl. No. 11/348,055, filed Oct. 25, 2013, Office Action.

\* cited by examiner

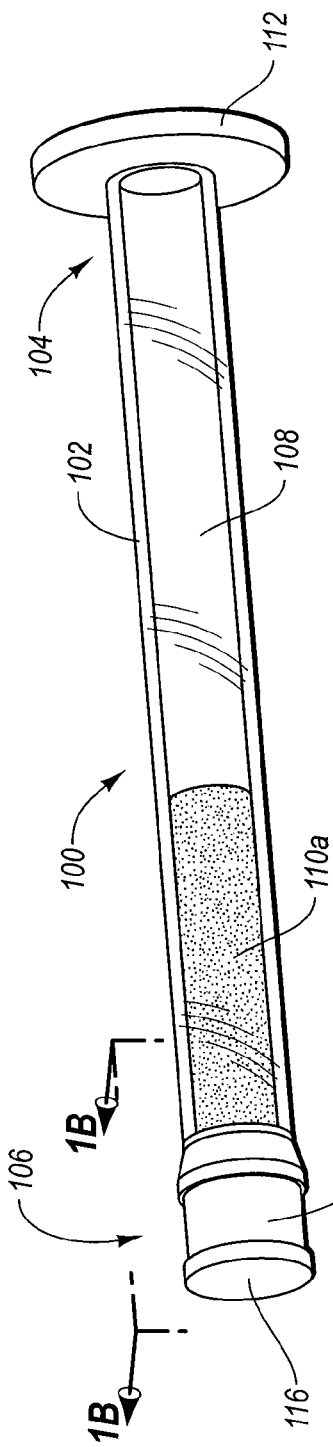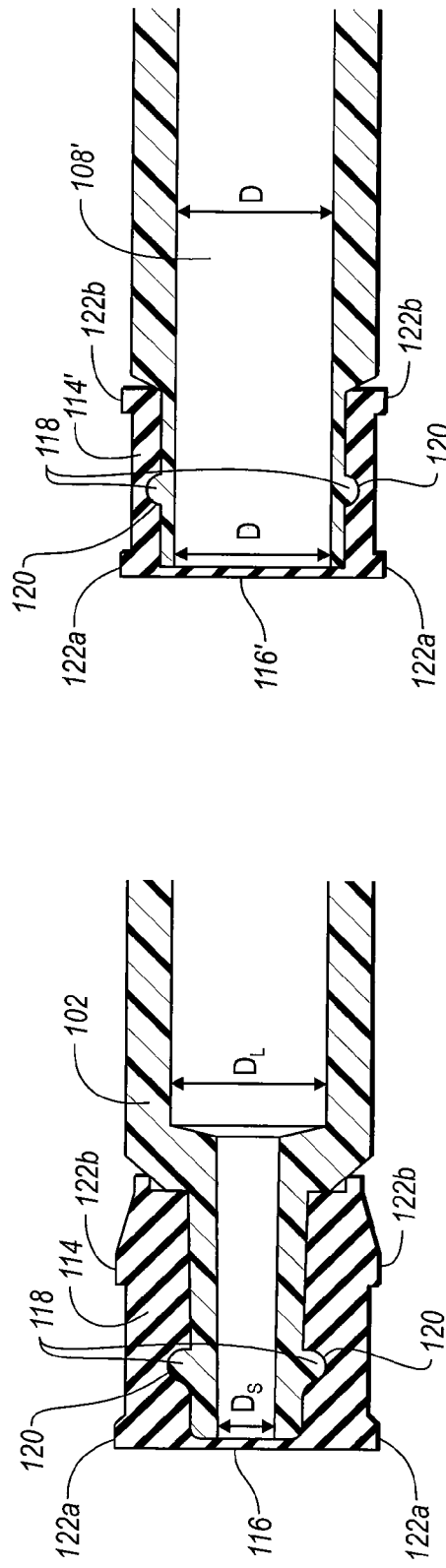

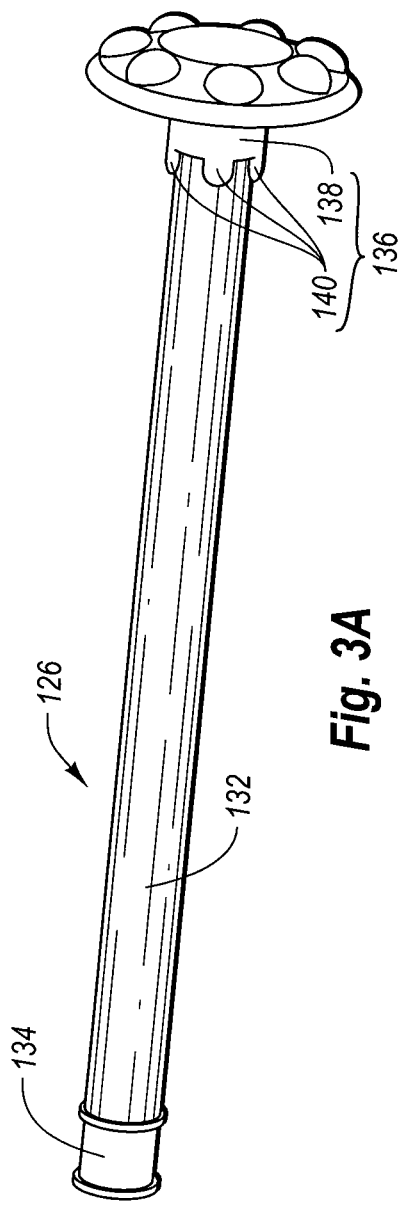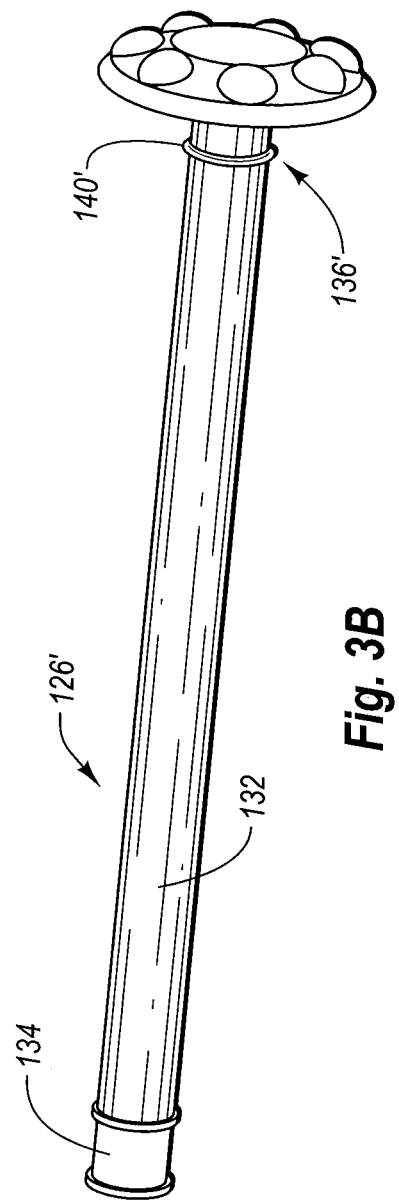

SYRINGE-TO-SYRINGE MIXING SYSTEMS AND RELATED APPARATUS AND METHODS

CROSS REFERENCE TO RELATED APPLICATIONS

This application is a continuation of U.S. application Ser. No. 12/525,961, filed Aug. 5, 2009, which is a national phase of International Application No. PCT/2007/067556, filed Apr. 26, 2007, which claims the benefit of U.S. patent application Ser. No. 11/673,334, filed Feb. 9, 2007. The disclosures of the foregoing are incorporated herein in their entirety.

BACKGROUND OF THE INVENTION

1. The Field of the Invention

The present application is directed to devices and methods for mixing, storing and dispensing two-part dental compositions.

2. The Relevant Technology

Many chemical formulations are packaged in two initially separate parts, often known as A and B components. Separate storage of the A and B components is often necessary where the composition resulting from mixing is unstable over time. For example, a self-etching dental primer composition may be provided in two initially separate parts to prevent the acid component from slowly destabilizing the polymerizable resin component by hydrolyzing off the functional group(s) to which the backbone of the resin is chemically bonded. Although such destabilization may not occur immediately upon mixing, with many such compositions, it is often recommended that the composition be used up or discarded within a certain time period (e.g., 30, 60, or 90 days) after initial mixing.

Because such compositions are unstable once mixed, it is important to ensure that the two parts remain separated prior to mixing, so as to prevent premature mixing and destabilization. In addition, it is awkward and time consuming for the practitioner to have to measure each component from a larger container, and then mix them together prior to introducing the mixed composition into a storage and/or dispensing device. In light of the above, it would be an advantage to provide a syringe-in-syringe all in one mixing and dispensing system for use with a two-part composition that would provide a practitioner with pre-measured amounts of each component ready for mixing, and that would provide the user with an all in one device that could easily be activated to effect mixing, while also being used to store and later dispense the composition. It would be a further advantage if the all-in-one mixing and dispensing device reduced the possibility of premature mixing of the components, while also being inexpensive and easy to mass manufacture so as to be disposable after a single use.

BRIEF SUMMARY OF THE PREFERRED EMBODIMENTS

The present invention is directed to a hollow inner plunger for use within a syringe-in-syringe mixing system for mixing a two-part dental composition. The hollow inner plunger includes a body having a continuous cylindrical wall defining an internal chamber for containing a first component. The body includes a proximal end and a distal end. A sealing plug and rupturable membrane are disposed at the distal end of the body, and the sealing plug and rupturable membrane are integrally formed together as a single piece (e.g., formed of a single piece of elastomeric material).

Providing a sealing plug and rupturable membrane that are integral so as to comprise a single piece of material greatly simplifies the mass manufacture of the hollow inner plunger and a syringe-in-syringe mixing system of which it forms a part. The integral sealing plug and rupturable membrane provide a simple, low-cost way to ensure initial separation of the two-parts of a two-part dental composition within the syringe-in-syringe mixing system, while also minimizing and/or preventing contamination that may otherwise occur if the rupturable membrane were to comprise a separate part bonded to the distal end of the hollow inner plunger.

For example, any bonding adhesive used to bond a membrane may be contaminated or chemically attacked by one or both of the components separated by the rupturable membrane causing weakening or failure of the bond (e.g., during storage). Furthermore, where the composition is introduced into the chamber prior to bonding of the rupturable membrane, the composition may contaminate the wall or other surface to which the membrane is to be bonded, which may inhibit formation of a strong bond. In addition, any bonding adhesive may likewise contaminate or chemically react with one or both of the two components to be separated, which may render the mixed composition less effective or otherwise unsuitable for use. Therefore, providing an integral sealing plug and rupturable membrane not only reduces the number of parts and steps required in assembly, but also reduces the likelihood of contamination of the two-part composition or any bonding adhesive.

The hollow inner plunger may comprise part of an associated syringe-in-syringe mixing system for use in mixing and dispensing a two-part dental composition. Such a system includes a first plunger, the hollow inner plunger as described above, and a syringe barrel configured to contain a second component. When assembled, the first plunger is slidably disposed in sealing engagement within the hollow inner plunger, and the hollow inner plunger is slidably disposed in sealing engagement within the syringe barrel. The first component is initially stored within the chamber of the inner hollow plunger separate from the second component which is stored within the chamber of the syringe barrel. The two chambers are initially separated by the rupturable membrane.

In one embodiment, the internal chamber of the hollow inner plunger has a diameter at the distal end of the body that is less than a diameter of the chamber at the proximal end. Preferably, this narrowing of diameter occurs near the distal end of the body (e.g., adjacent to or near a proximal end of the integral sealing plug/rupturable membrane). Narrowing the diameter of the chamber significantly increases the pressure exerted by the first component against the rupturable membrane, which has been found to greatly aid in causing rupture of the membrane in such a way that results in jetting of the first component into the second component. The result of such jetting action is near instantaneous mixing of the two components, particularly for two relatively low viscosity liquids. As such, the internal diameter at the distal end is preferably not more than about 75% of the largest diameter of the chamber (e.g., the diameter at the proximal end), more preferably not more than about 50% of the largest diameter of the chamber (e.g., the diameter at the proximal end), and most preferably not more than about 35% of the largest diameter (e.g., the diameter at the proximal end). The inventors have found that a diameter at the distal end (i.e., adjacent the rupturable membrane) measuring about one-third that of the largest diameter of the chamber (e.g., the diameter from the proximal end to a location adjacent the sealing plug where the diameter is abruptly narrowed) results in catastrophic rupture of the membrane and jetting of substantially all of the first component through the rupturable membrane and into the second component to effect homogeneous mixing.

The actual thickness of the rupturable membrane depends on the strength and other physical properties of the selected material, along with the configuration of any reduction in diameter leading up to the proximal end of the body where the membrane is located. The rupturable membrane preferably has a thickness ranging from about 0.0005 inch to about 0.04 inch, more preferably from about 0.002 inch to about 0.025 inch, and most preferably from about 0.005 inch to about 0.015 inch. For example, it has been found that a thermoplastic elastomer material having a thickness from about 0.005 inch to about 0.010 inch is particularly preferred for the reasons described above when the diameter of the internal chamber is reduced adjacent the distal end to about one-third of its value at the proximal end.

These and other advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 1A is a perspective view of an exemplary hollow inner plunger including an integrally formed sealing plug and rupturable membrane;

FIG. 1B is a close up cross-sectional view of a distal end of the hollow inner plunger including the integral sealing plug and rupturable membrane of FIG. 1A;

FIG. 1C is a close up cross-sectional view of an alternative hollow inner plunger including an internal chamber of substantially constant diameter along its entire length;

FIG. 3A is a perspective view of an exemplary first plunger for use in a syringe-in-syringe mixing system, the first plunger including an exemplary locking mechanism to prevent pull-out of the first plunger once it has been fully inserted within the hollow inner plunger;

FIG. 3B is a perspective view of an alternative first plunger including an alternative locking mechanism;

DETAILED DESCRIPTION OF THE PREFERRED EMBODIMENTS

I. Introduction

Figure 2:
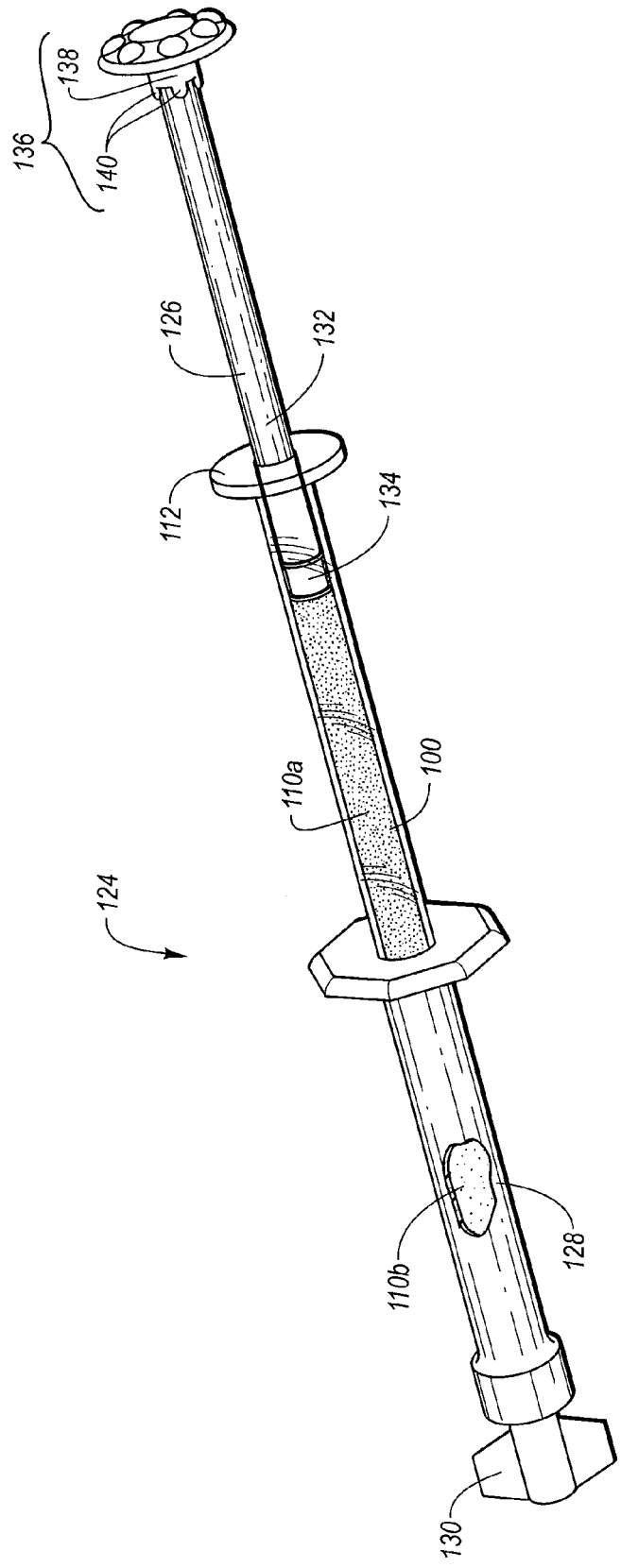
FIG. 2 is a perspective view of an exemplary syringe-in-syringe mixing system incorporating a hollow inner plunger according to the present invention.

In one aspect, the present invention is directed to a hollow inner plunger for use within a syringe-in-syringe mixing system for mixing a two-part dental composition. The hollow inner plunger includes a body having a continuous cylindrical wall defining an internal chamber for containing a first component. The body includes a proximal end and a distal end. A sealing plug and rupturable membrane are disposed at the distal end of the body, and the sealing plug and rupturable membrane are integrally formed together as a single piece (e.g., formed of a single piece of elastomeric material).

The hollow inner plunger may comprise part of an associated syringe-in-syringe mixing system for use in mixing and dispensing a two-part dental composition. Such a system includes a first plunger, the hollow inner plunger as described above, and a syringe barrel configured to contain a second component. When assembled, the first plunger is slidably disposed in sealing engagement within the hollow inner plunger, and the hollow inner plunger is slidably disposed in sealing engagement within the syringe barrel. The first component is initially stored within the chamber of the inner hollow plunger separate from the second component which is stored within the chamber of the syringe barrel. The two chambers are initially separated by the rupturable membrane.

II. Exemplary Hollow Inner Plungers

FIG. 1A is a perspective view of hollow inner plunger 100 having a body including a continuous cylindrical wall 102. The body and wall 102 include a proximal end 104 and an opposite distal end 106. The interior of wall 102 defines an internal chamber 108 configured to contain a first component 110a. A flange 112 is disposed at proximal end 104, while an integrally formed sealing plug and rupturable membrane 116 is disposed at distal end 106. Advantageously, and as shown in FIG. 1B, sealing plug 114 and membrane 116 are integrally formed as a single piece, for example, from an elastomeric material. Rupturable membrane 116 caps and seals off the distal end of hollow inner plunger 100 so as to contain first component 110a within chamber 108, keeping it separate from a second component until the user desires to effect mixing. Sealing plug 114 is disposed on the outside of body wall 102 and is configured to plug within a syringe barrel (see FIG. 2) so as to seal the proximal end of the syringe barrel when the hollow inner plunger 100 is assembled into a syringe-in-syringe mixing system.

The distal portion of the body of hollow inner plunger 100 over which sealing plug 114 is fitted advantageously includes an outwardly extending annular ridge 118 that prevents plug 114 from being separated from hollow inner plunger 100 during rupture of rupturable membrane 116. Sealing plug 114 includes a corresponding annular groove 120 configured to matingly engage ridge 118 so as to securely attach sealing plug and rupturable membrane 116 to the body of hollow inner plunger 100.

Sealing plug 114 and rupturable membrane 116 may advantageously be formed of an elastomeric material (e.g., a thermoset elastomer or thermoplastic elastomer), which advantageously provides an excellent seal against a syringe barrel while also providing a desired strength to rupturable membrane 116. Rupturable membrane 116 seals off the distal end of hollow inner plunger 100, separating first component 110a from a second component 110b contained within a syringe barrel 128 (see FIG. 2) until the user intentionally ruptures membrane 116, causing first component 110a to be forced into syringe barrel 128, where the two components are mixed together.

Providing a sealing plug 114 and rupturable membrane 116 that are integral so as to comprise a single piece of material greatly simplifies the mass manufacture of the hollow inner plunger 100 and a syringe-in-syringe mixing system of which it forms a part. The integral sealing plug 114 and rupturable membrane 116 provide a simple, low-cost way to ensure initial separation of the two-parts of a two-part dental composition within a syringe-in-syringe mixing system, while also minimizing and/or preventing contamination that may otherwise occur if the rupturable membrane 116 and sealing plug 114 were to comprise two separate parts requiring bonding of each to the body or wall 102.

For example, any bonding adhesive used to bond a rupturable membrane to wall 102 (or any other structure) may be contaminated or chemically attacked by one or both of the components separated by the rupturable membrane (e.g., during storage). Such contamination or chemical reaction would likely lead to weakening and/or failure of the bond holding the membrane in place. Furthermore, where the composition is introduced into the chamber prior to bonding of the rupturable membrane, the composition may contaminate the wall or other surface to which the membrane is to be bonded, which may inhibit formation of a good bond.

In addition, any bonding adhesive may likewise contaminate or chemically react with one or both of the two components intended for separation within a syringe-in-syringe mixing system, which may render one component, both components, or the mixed composition less effective or otherwise unsuitable for use. Therefore, providing an integral sealing plug and rupturable membrane not only reduces the number of parts and steps required to assemble a hollow inner plunger and an associated syringe-in-syringe mixing system, but also reduces the likelihood of contamination of the two-part composition or any bonding adhesive, either of which could render the mixing system and/or composition useless.

FIGS. 1B and 1C illustrate cross-sectional views of alternative embodiments. FIG. 1B illustrates an example in which the inside diameter of the chamber 108 is reduced adjacent to rupturable membrane 116, while FIG. 1C illustrates an alternative example in which the diameter D of the chamber 108' is not reduced, but is substantially constant along the length of the chamber 108' so that the diameter D adjacent membrane 116' and plug 114' is substantially the same as the diameter D elsewhere along chamber 108'.

FIG. 1B shows a preferred embodiment in which the internal chamber 108 of hollow inner plunger 100 has a diameter $D_S$ at distal end 106 of the body that is less than a diameter $D_L$ of the chamber at proximal end 104. As illustrated, preferably this narrowing of diameter occurs near the distal end 106 of the body. For example, in the illustrated embodiment, the narrowing of the chamber diameter occurs adjacent or near the proximal edge of the sealing plug 114. Reducing the outside diameter of the body wall 102 along this distal portion also provides space for the receipt of sealing plug 114 in a way that presents an overall outside diameter of the plunger 100 that is substantially constant along the entire length (i.e., between proximal end 104 adjacent flange 112 and distal end 106), with the exception of primary and secondary sealing surfaces 122a and 122b, respectively, which are configured to seal against the inside surface of a syringe barrel. Such an arrangement provides a tight fit of the inner plunger 100 within a syringe barrel (e.g., see FIG. 2), reducing any tendency of the inner plunger to wobble within the syringe barrel, which tendency may become particularly pronounced further away from the sealing surfaces 122a and 122b (e.g., near proximal end 104).

In addition, narrowing the diameter of chamber 108 significantly increases the pressure exerted by first component 110a against rupturable membrane 116, when force is selectively applied by a user to a plunger inserted within proximal end 104. Narrowing of diameter has been found to greatly aid in causing rupture of membrane 116 in such a way that results in jetting of first component 110a into second component 110b. The result of such jetting action is near instantaneous mixing of the two components, particularly for two relatively low viscosity liquids.

As such, the internal diameter $D_S$ at the distal end 106 is preferably not more than about 75% of the diameter $D_L$ at proximal end 104 and along the remainder of chamber 108, more preferably not more than about 50% of the diameter $D_L$, and most preferably not more than about 35% of the diameter $D_L$. The inventors have found that a diameter at the distal end (i.e., adjacent the rupturable membrane) measuring about one-third that of the largest diameter of the chamber (e.g., the diameter is substantially constant from the proximal end 104 to a location adjacent the sealing plug 114 where the diameter is abruptly narrowed) results in catastrophic rupture of the membrane and jetting of substantially all of the first component 110a through the rupturable membrane 116 and into the second component to effect homogeneous mixing.

The actual thickness of rupturable membrane 116 depends on the strength and other physical properties of the selected material, along with the configuration of any reduction in diameter leading up to the proximal end of the body where the membrane is located. The rupturable membrane preferably has a thickness ranging from about 0.0005 inch to about 0.04 inch, more preferably from about 0.002 inch to about 0.025 inch, and most preferably from about 0.005 inch to about 0.015 inch. For example, it has been found that a rupturable membrane formed of a thermoplastic elastomer material having a thickness from about 0.005 inch to about 0.010 inch is particularly preferred for the reasons described above when the diameter $D_S$ of the internal chamber 108 is reduced adjacent the distal end 106 to about one-third of its value at the proximal end 104.

III. Exemplary Syringe-in-Syringe and Syringe-to-Syringe Mixing Systems

FIG. 2 illustrates an exemplary syringe-in-syringe mixing system 124. System 124 includes a first plunger 126, a hollow inner plunger 100, and a syringe barrel 128 with a cap 130 at a distal end of syringe barrel 128 (a plug fitting inside the distal end of barrel 128 could equivalently be used). First plunger 126 is slidably disposed within hollow inner plunger 100, which is slidably disposed within syringe barrel 128. As illustrated, hollow inner plunger 100 contains a first component 110a, and syringe barrel 128 contains a second component 110b. First plunger 126 includes an elongate stem 132 and an associated sealing plug 134 at a distal end of stem 132.

As perhaps best seen in FIG. 3A, a locking mechanism 136 may advantageously be included near a proximal end of first plunger 126 to prevent withdrawal of first plunger 126 from inner plunger 100 once inserted. Such a locking mechanism is helpful as once the membrane is ruptured, the device cannot be reused for mixing two components, although it can be used to dispense the mixed composition until all has been dispensed. Locking first plunger within inner plunger 100 allows the dispensing device to operate as a syringe comprising a barrel and plunger, which simplifies dispensing by the user while also preventing slideout of the first plunger, which could result in loss, contamination or waste of the mixed composition. Illustrated locking mechanism 136 comprises a circumferentially extending portion of enlarged diameter 138 (relative to the remainder of stem 132), with a plurality of longitudinally extending interlock ribs 140. In use, interlock ribs 140 are inserted into hollow inner plunger 100, where the ribs 140 bias against the inside wall 102 of hollow inner plunger 100. The system is configured such that when first plunger 126 is fully inserted into hollow inner plunger 100, circumferentially extending portion 138 rests within flange 112 of hollow inner plunger 100, while interlock ribs 140 extend distally into hollow inner plunger 100, past flange 112. Because flange 112 provides increased barrel strength relative to the remainder of hollow inner plunger 100, little or no deformation occurs to the inside wall of hollow inner plunger 100 on account of portion 138, but deformation is caused by ribs 140, resulting in associated indentations being formed into the inside wall 102 of hollow plunger 100 distal to flange 112, preventing, or at least inhibiting, later removal of first plunger 126 from hollow inner plunger 100 (e.g., see FIG. 4D).

FIG. 3B illustrates an alternative first plunger 126' including a cylindrical elongate stem 132, and a sealing plug 134. The principle difference between the first plunger 126' and first plunger 126 of FIG. 3A and FIG. 2 is that first plunger 126' includes an alternative locking mechanism 136' comprising an annular interlock ring 140' rather than the enlarged diameter portion 138 and plurality of interlock ribs 140 of the embodiment of FIG. 3A. Similar to interlock ribs 140, annular interlock ring 140' causes the formation of an indentation or groove within the inside wall 102 of hollow inner plunger 100. Annular interlock ring 140' resides in the formed groove, preventing, or at least inhibiting, pull out of first plunger 126 once fully inserted into hollow inner plunger 100. Other locking mechanisms (e.g., an interference fit of the first plunger into the hollow inner plunger) may alternatively be used.

According to one method, a pre-measured, pre-filled syringe-in-syringe mixing system (as shown in FIG. 2) may be manufactured by first inserting first plunger 126 into hollow inner plunger 100 so that first plunger 126 is slidably received within hollow inner plunger 100. Sealing plug 134 of first plunger 126 seals the proximal end of hollow inner plunger. First component 110a may then be introduced into internal chamber 108 of hollow inner plunger 100. Integrally formed rupturable membrane 116 and sealing plug 114 may then be placed over distal end 106 of hollow inner plunger 100, effectively sealing first component 110a within chamber 108. Next, hollow inner plunger 100 may be inserted into syringe barrel 128 so that hollow inner plunger 100 is slidably received therein. Primary and secondary sealing surfaces 122a and 122b, respectively, form a seal to prevent passage of any fluid around seal 114, while membrane 116 forms a seal to prevent passage of any fluid through seal 114 until the membrane is intentionally ruptured by the user. Second component 110b may then be introduced into syringe barrel 128 through the distal end of the barrel. Cap 130 may finally be placed over the distal end of barrel 128 so as to seal the distal end. Assembly in such a manner prevents or at least minimizes the formation and entrapment of air bubbles within the chamber of the inner plunger 100 and/or the syringe barrel 128, and is thus currently preferred.

Figure 3C:
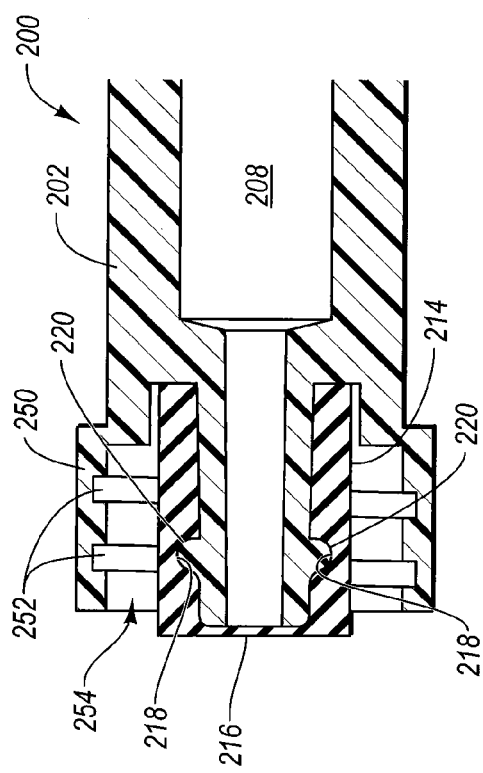
FIGS. 3C-3D illustrate an alternative embodiment in which the integral sealing plug and rupturable membrane may be incorporated within a syringe-to-syringe mixing system.
Figure 3D:
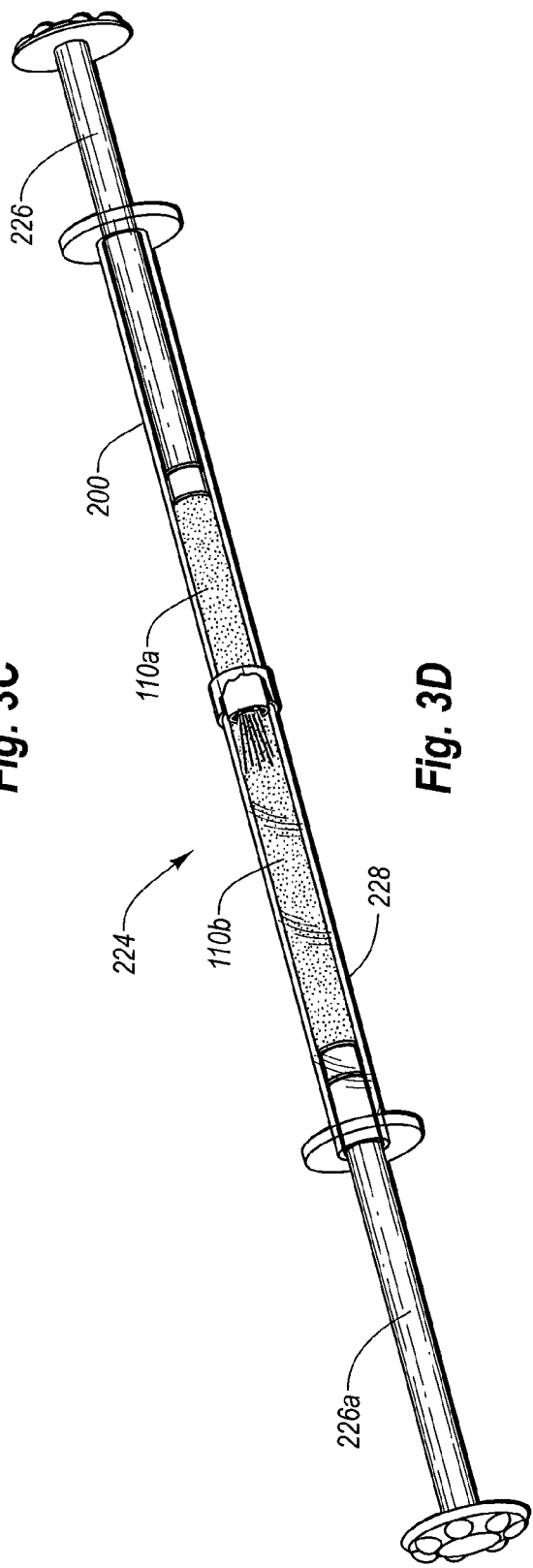

FIGS. 3C-3D illustrate an alternative embodiment in which the integral sealing plug and rupturable membrane may be incorporated within a syringe-to-syringe mixing system 224. FIG. 3C illustrates a cross-sectional view of alternative syringe barrel 200 similar to those illustrated in FIGS. 1B-1C including a continuous cylindrical wall 202 which defines an internal chamber 208 configured to contain a first component. The principal difference of alternative syringe barrel 200 relative to those illustrated in FIGS. 1B and 1C is that syringe barrel 200 is not configured to slide within a syringe barrel, but rather to be coupled to another syringe barrel so as to allow syringe-to-syringe mixing (as opposed to syringe-in-syringe mixing), as shown in FIG. 3D.

Syringe barrel 200 includes means for coupling to another syringe barrel. In the illustrated embodiment, a female portion of a coupling mechanism is disposed at the distal end of barrel 200. A cylindrical outer wall 250 with grooves 252 formed therein acts to receive a correspondingly shaped male portion of another syringe barrel, which is received within cylindrically extending cavity 254. The male portion includes threads configured to engage within grooves 252. A male portion of a coupling mechanism may alternatively be disposed at the distal end of syringe barrel 200 which includes the integrally formed rupturable membrane and sealing plug, with the female portion being disposed on the other syringe. Other coupling means and mechanisms will be apparent to one skilled in the art.

Similar to hollow inner plunger 100, syringe barrel 200 also includes a rupturable membrane 216, a sealing plug 214, an outwardly extending annular ridge 218, and annular groove 220. Rupturable membrane 216 caps and seals off the distal end of syringe barrel 200 so as to contain a first component within chamber 208, keeping it separate from a second component until the user desires to effect mixing. Sealing plug 214 is disposed on the outside of body wall 202, and although it does not slide or provide a seal against the inside of a syringe barrel (as in a syringe-in-syringe mixing system), its presence may help to seal and prevent any leaking that may otherwise occur between the two syringes when they are coupled together. In addition, such a sealing plug formed of an elastomeric material (e.g., a thermoplastic elastomer material) may improve the tightness, grip, and coupling strength of syringe barrel 200 to another syringe barrel, as the male portion of the other syringe barrel contacts sealing plug 214 (i.e., plug 214 may increase coupling friction by contacting or gripping the male portion of the coupled syringe barrel). In addition, such an integral sealing plug and rupturable membrane, specifically the arrangement of annular ridge 218 and annular groove 220, provides means for attaching rupturable membrane 216 to syringe barrel 200 without the need for glue or any other adhesive, which is helpful in preventing contamination as described above.

When it is desired to effect mixing of the two-part composition, the user presses first plunger 226 into syringe barrel 200 so as to compress first component 110a. Although it may be possible to first press opposite plunger 226a, this is less preferred as it may reduce the jetting mixing action of one component into the other. First plunger 226 may include a mark label thereon indicating that it be pressed first (not shown). Once a sufficient force is applied, rupturable membrane 216 breaks, causing first component 110a to be expressed under pressure from syringe barrel 200 into syringe barrel 228 where it mixes with second component 110b.

The force of such rupture and jetting of the first component 110a into the second component 110b is often sufficient to effect homogeneous mixing, such that no additional mixing is required, although the illustrated syringe-to-syringe mixing system 224 easily allows a user to alternatingly press plungers 226 and 226a so as to further mix the two components together. Such a syringe-to-syringe mixing system may be particularly preferred where one or both components are of particularly high viscosity, such that additional mixing may be needed.

III. Exemplary Method of Use

Figure 4A:
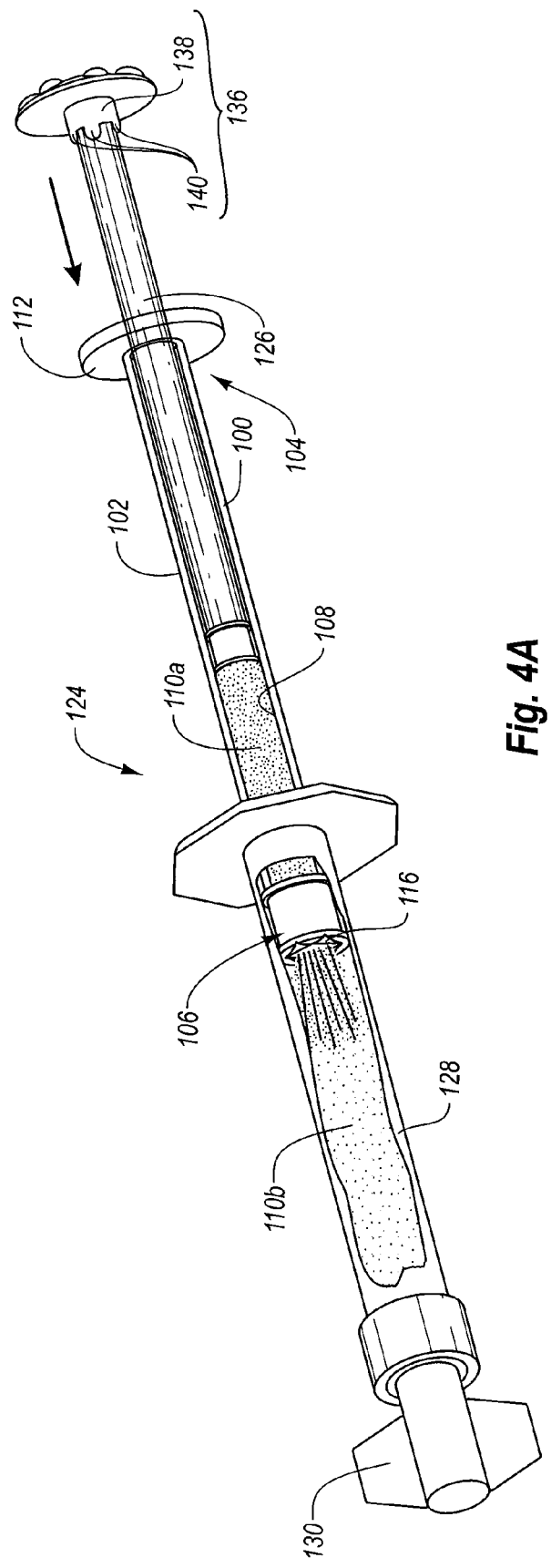
FIG. 4A illustrates the first plunger being pressed into the hollow inner plunger so as to cause the rupturable membrane at the distal end of the hollow inner plunger to break, resulting in jet mixing of the first component into the second component.

FIG. 4A illustrates an exemplary syringe-in-syringe mixing system 124. When it is desired to effect mixing of the two-part composition, the user may press first plunger 126 into hollow inner plunger 100 so as to compress first component 110a. Once a sufficient force is applied, rupturable membrane 116 breaks causing first component 110a to be expressed under pressure from hollow inner plunger 100 into syringe barrel 128 where it mixes with second component 110b.

The force of such rupture and jetting of the first component 110a into the second component 110b is sufficient to effect homogeneous mixing, such that no additional mixing (e.g., by shaking) is required, particularly where both components are low viscosity liquids. Although preferred for use with liquid-liquid systems, first and second components 110a and 110b may each be a liquid, or one may be a solid powder, as dictated by the characteristics of the two-part composition to be mixed. The syringe-in-syringe mixer is particularly well suited for mixing together two relatively low viscosity liquids (e.g., less than about 100 centipoise, more preferably less than about 10 centipoise, and most preferably less than about 3 centipoise), because of the ability of the system to cause one component to be forcefully ejected into the other component so as to effect mixing without any additional effort (e.g., shaking is not necessary). One contemplated relatively low viscosity liquid-liquid two-part composition is a two-part self etching dental primer composition described in U.S. patent application Ser. No. 11/261,171, filed Oct. 28, 2005, and entitled SELF-ETCHING DENTAL PRIMER COMPOSITIONS AND METHODS AND SYSTEMS UTILIZING SUCH COMPOSITIONS.

Although particularly well suited for use with lower viscosity liquids, the system may also be used with higher viscosity liquids (e.g., up to about 1000 centipoise or even up to about 3500 centipoise) or a liquid-solid powder two-part composition, although when used for mixing such two-part compositions further mixing beyond that provided by the rupture of the membrane and turbulent jetting of one component into the other may be necessary. For example, it may be helpful when mixing such a composition to remove cap 130 and couple the system to another syringe so as to allow syringe-to-syringe mixing of the composition.

In other words, the rupturable membrane 116 is configured to only pass first component 110a for mixing with second component 110b under a pressure sufficiently high to cause jetting of the first component into the second component (e.g., so as to create turbulence sufficient to mix the two components together). Cap 130 may include a check-valve or other vent (not shown) that permits air or other gas within barrel 128 to be expelled as first component 110a is expressed into barrel 128. Any check-valve known in the art can be used or modified to attach to barrel 128.

Figure 4B:
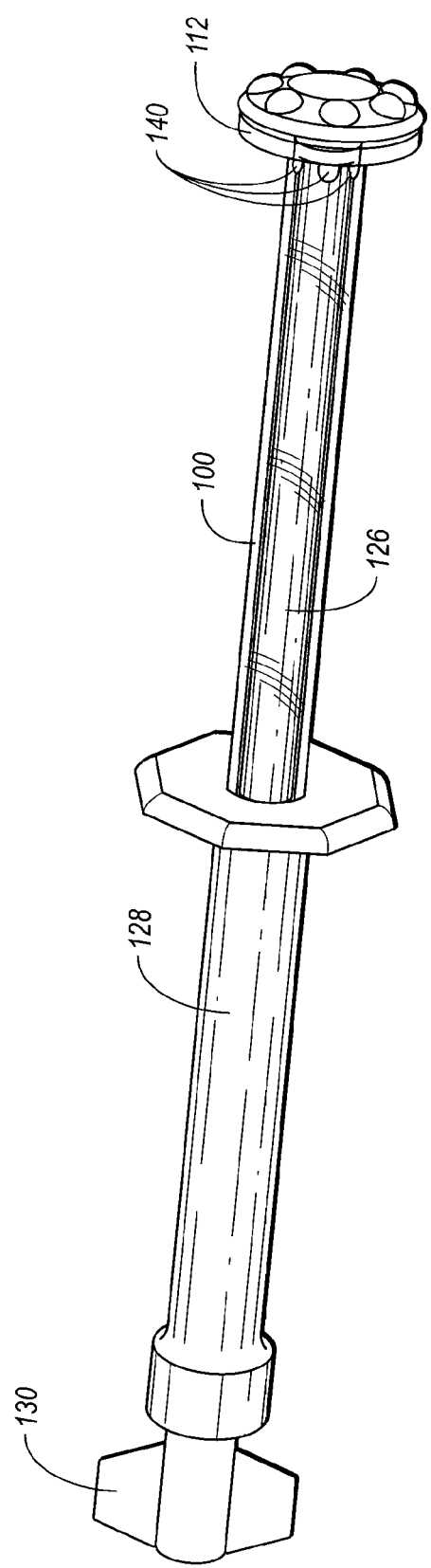
FIG. 4B illustrates the first plunger in a locked configuration relative to the hollow inner plunger so as to prevent pull-out of the first plunger from the hollow inner plunger.

The system may advantageously be configured such that a force required to rupture membrane 116 is approximately equal to a force required to insert and lock locking mechanism 136 (i.e., enlarged diameter portion 138 and interlocking ribs 140) of the cylindrical elongate stem 132 into hollow inner plunger 100, although it is not required. Such a configuration provides a smooth and continuous movement and feel during use of the system as first plunger 126 is pressed into hollow inner plunger 100, rupturing membrane 116 and locking first plunger 126 into hollow inner plunger 100, all within a single movement. FIG. 4B illustrates the system once first plunger 126 has been fully inserted into hollow inner plunger 100. In this configuration, first plunger 126 is locked into hollow inner plunger 100.

In the locked configuration as shown, it is difficult, if not impossible, to withdraw first plunger 126 from hollow inner plunger 100 without destroying the system. Enlarged diameter portion 138 is disposed within the center of flange 112, while ribs 140 extend distally from flange 112 further into hollow inner plunger 100. Because flange 112 has increased barrel strength relative to the area of hollow inner plunger 100 immediately distal to flange 112, the inside wall surface 102 of hollow inner plunger will be deformed by ribs 140 so as to form a depression into the portion of the contacted inside wall 102. At the same time, the inside wall surface 102 of hollow inner plunger 100 directly under flange 112 will be deformed only slightly if at all because of the increased barrel strength of the flange region 112 compared to the region contacted by ribs 140. In other words, ribs 140 create an interlock with the inside surface of hollow inner plunger 100, preventing, or at least inhibiting, subsequent withdrawal of first plunger 126 from hollow inner plunger 100.

Figure 4C:
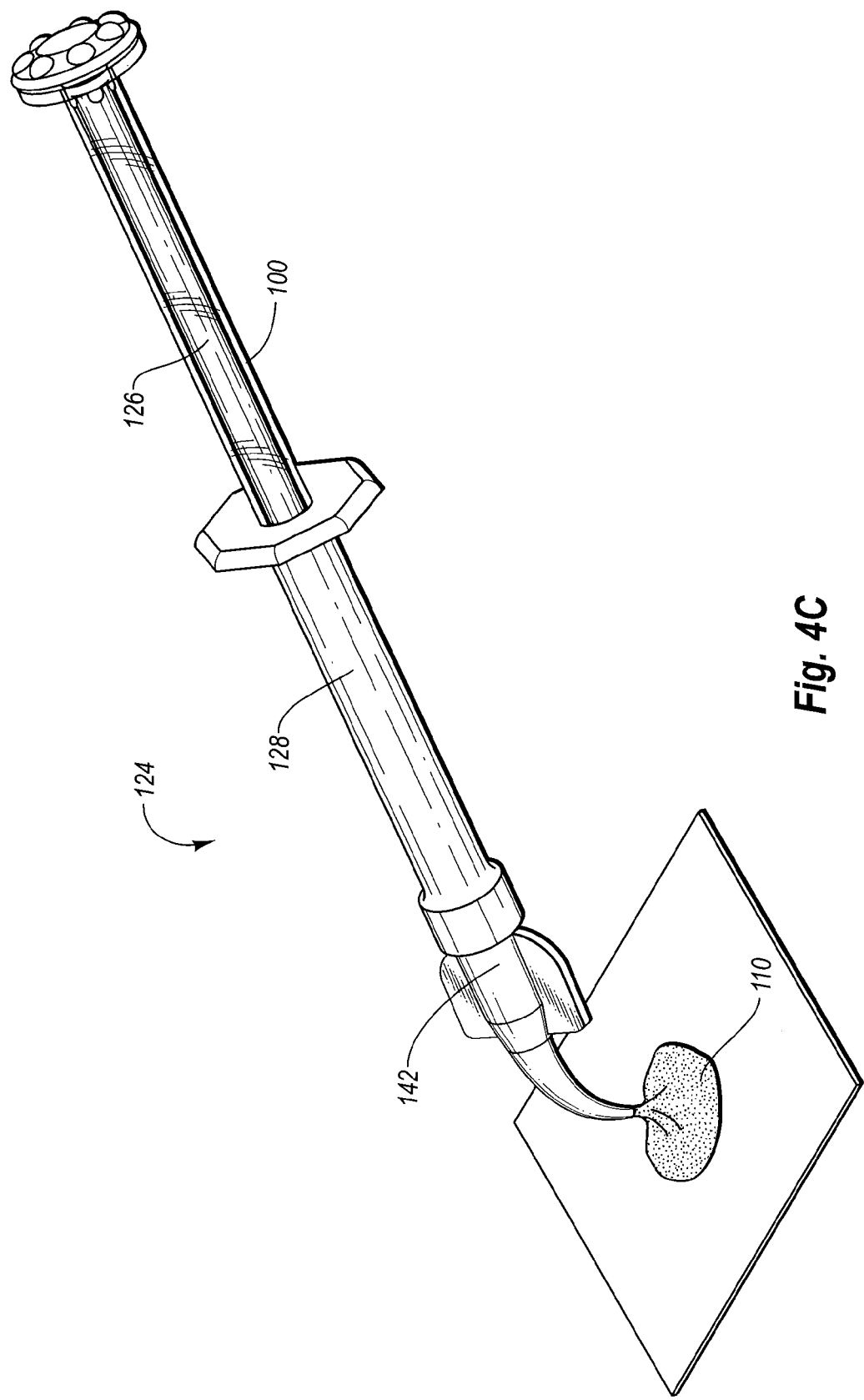
FIG. 4C illustrates dispensing of a portion of the mixed two-part composition onto a pad for subsequent application to a desired surface.

FIG. 4C illustrates the system 124 with a dispensing tip 142 coupled at a distal end of barrel 128 so as to allow the user to dispense the mixed two-part composition 110. As illustrated, composition 110 maybe dispensed onto a pad for subsequent application (e.g., with a brush tool). Alternatively composition 110 may be dispensed directly onto a tooth or other surface, depending on the preference of the user.

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A syringe-to-syringe mixing system comprising:
   a first syringe barrel comprised of:
   a hollow body including a continuous cylindrical wall defining an internal chamber for containing a first component, the hollow body having a proximal end and a distal dispensing end;
   only a single orifice at the distal dispensing end of the hollow body through which the first component contained in the internal chamber can be dispensed; and
   a rupturable membrane disposed at the distal dispensing end of the hollow body and which caps and seals off the single orifice until irreversible rupture of the rupturable membrane by application of sufficient pressure on the first component contained in the internal chamber so as to irreversibly rupture the rupturable membrane, wherein the rupturable membrane has a cross-sectional thickness that facilitates rupture of the rupturable membrane during use;
   a first plunger slidably disposed within the hollow body of the first syringe barrel for applying pressure to a first component within the internal chamber;
   a second syringe barrel having a distal dispensing end that is couplable to the distal dispensing end of the hollow body of the first syringe barrel; and a second plunger slidably disposed within the second syringe barrel for applying pressure to a second component within the second internal chamber of the second syringe barrel.

2. A syringe-to-syringe mixing system as in claim 1, wherein the rupturable membrane comprises an elastomeric material.

3. A syringe-to-syringe mixing system as in claim 1, wherein the rupturable membrane comprises a thermoplastic elastomer or a thermoset elastomer.

4. A syringe-to-syringe mixing system as in claim 1, wherein the rupturable membrane has a thickness between about 0.0005 inch and about 0.04 inch.

5. A syringe-to-syringe mixing system as in claim 1, wherein the rupturable membrane has a thickness between about 0.002 inch and about 0.025 inch.

6. A syringe-to-syringe mixing system as in claim 1, wherein the rupturable membrane has a thickness between about 0.005 inch and about 0.015 inch.

7. A syringe-to-syringe mixing system as in claim 1, further comprising a flange disposed at the proximal end of the hollow body of the first syringe barrel.

8. A syringe-to-syringe mixing system as in claim 1, further comprising an outwardly extending annular ridge disposed near the distal end of the hollow body of the first syringe barrel and a sealing plug attached to the rupturable membrane and having a corresponding annular groove configured to matingly engage the annular ridge so as to attach the sealing plug and rupturable membrane to the hollow body of the first syringe barrel.

9. A syringe-to-syringe mixing system as in claim 1, further comprising:
   a first component of a two-component composition initially contained within the internal chamber of the hollow body of the first syringe barrel; and
   a second component of the two-component composition initially contained within an internal chamber of the second syringe barrel.

10. A syringe-to-syringe mixing system as in claim 1, further comprising coupling means disposed at the distal dispensing end of the hollow body for coupling the first syringe barrel to the second syringe barrel.

11. A syringe-to-syringe mixing system as in claim 10, wherein the coupling means comprises a female portion of a coupling mechanism, including a cylindrical outer wall with grooves formed therein, configured to receive a correspondingly shaped male portion of the second syringe barrel.

12. A syringe-to-syringe mixing system as in claim 10, wherein the coupling means comprises a male portion of a coupling mechanism, including raised threads formed therein, configured to be received within a correspondingly shaped female portion of the second syringe barrel.

13. A syringe-to-syringe mixing system as in claim 1, wherein the internal chamber of the first syringe barrel has a diameter at the distal end of the body that is less than a diameter of the internal chamber at the proximal end of the hollow body.

14. A syringe-to-syringe mixing system as in claim 13, wherein the internal chamber has a diameter at the distal end of the hollow body that is not more than about 75% of a diameter of the internal chamber at the proximal end.

15. A syringe-to-syringe mixing system as in claim 13, wherein the internal chamber has a diameter at the distal end of the hollow body that is not more than about 50% of a diameter of the internal chamber at the proximal end.

16. A syringe-to-syringe mixing system as in claim 13, wherein the internal chamber has a diameter at the distal end of the hollow body that is not more than about 35% of a diameter of the internal chamber at the proximal end.

17. A syringe-in-syringe mixing system comprising:
   a first syringe barrel comprised of:
      a hollow body including a continuous cylindrical wall defining an internal chamber for containing a first component, the hollow body having a proximal end and a distal dispensing end;
      only a single orifice at the distal dispensing end of the hollow body through which the first component contained in the internal chamber can be dispensed; and
      a rupturable membrane disposed at the distal dispensing end of the hollow body and which caps and seals off the single orifice until irreversible rupture of the rupturable membrane by application of sufficient pressure on the first component contained in the internal chamber so as to irreversibly rupture the rupturable membrane, wherein the rupturable membrane has a cross-sectional thickness that facilitates rupture of the rupturable membrane during use;
   a plunger slidably disposed within the hollow body of the first syringe barrel for applying pressure to a first component within the internal chamber;
   a sealing plug disposed at the distal dispensing end of the hollow body of the first syringe barrel and which cooperates with the rupturable membrane to form a sealing plug-rupturable membrane body; and
   a second syringe barrel having a second internal chamber configured to slidably receive the hollow syringe barrel therein so that the sealing plug sealingly engages an interior wall of the second syringe barrel defining the second internal chamber,
   wherein the hollow syringe barrel is slidably received within the second internal chamber of the second syringe barrel and acts as a second plunger during use for applying pressure to a mixed composition contained within the second internal chamber of the second syringe barrel.

18. A syringe-in-syringe mixing system as in claim 17, further comprising:
   a first component of a two-component composition initially contained within the internal chamber of the hollow body of the first syringe barrel; and
   a second component of the two-component composition initially contained within the second internal chamber of the second syringe barrel.

19. A hollow syringe barrel for use within a syringe-to-syringe mixing system for mixing a two-part composition, the syringe barrel comprising:
   a hollow body including a continuous cylindrical wall defining an internal chamber for containing a first component, the hollow body having a proximal end and a distal dispensing end with only a single orifice through which a first component in the internal chamber can be dispensed;
   a rupturable membrane disposed at the distal dispensing end of the body so as to cap and seal off the single orifice until irreversible rupture of the rupturable membrane by application of sufficient pressure on a first component contained in the internal chamber so as to irreversibly rupture the rupturable membrane, wherein the rupturable membrane has a cross-sectional thickness to facilitate rupture of the rupturable membrane during use; and
   coupling means disposed at the distal dispensing end of the hollow body for coupling the syringe barrel to a distal dispensing end of another syringe barrel so as to allow for syringe-to-syringe mixing.

20. A hollow syringe barrel as in claim 19, wherein the coupling means comprises a female portion of a coupling mechanism, including a cylindrical outer wall with grooves formed in an interior surface of the outer wall, configured to receive a correspondingly shaped male portion at a distal dispending end of another syringe barrel.

21. A hollow syringe barrel as in claim 19, wherein the coupling means comprises a male portion of a coupling mechanism, including raised threads formed on an exterior surface of the male portion, configured to be received within a correspondingly shaped female portion of at a distal dispending end another syringe barrel.

22. A hollow syringe barrel as in claim 19, wherein the internal chamber has a diameter at the distal end of the hollow body that is less than a diameter of the internal chamber at the proximal end of the hollow body.

23. A hollow syringe barrel as in claim 19, wherein the rupturable membrane comprises an elastomeric material and has a thickness between about 0.0005 inch and about 0.04 inch.

24. A hollow syringe barrel as recited in claim 19, further comprising an outwardly extending annular ridge disposed near the distal dispensing end of the hollow body and a sealing plug attached to the rupturable membrane and having a corresponding annular groove configured to matingly engage and enclose the annular ridge so as to attach the sealing plug and rupturable membrane to the hollow body of the hollow syringe barrel.

25. A syringe-to-syringe mixing system comprising:
a hollow syringe barrel as recited in claim 19; and
a second syringe barrel having a distal dispensing end that is couplable by the coupling means to the distal dispensing end of the hollow body of the hollow syringe barrel.

26. A syringe-to-syringe mixing system as in claim 25, further comprising:
a first component of a two-component composition initially contained within the internal chamber of the hollow body of the hollow syringe barrel;
a first plunger slidably disposed within the hollow body of the hollow syringe barrel for applying pressure to the first component within the internal chamber;
a second component of the two-component composition initially contained within a second internal chamber of the second syringe barrel; and
a second plunger slidably disposed within the second syringe barrel for applying pressure to the second component within the second internal chamber of the second syringe barrel.

27. A syringe-in-syringe mixing system for use in mixing a two-part dental composition comprising:
a first plunger;
a hollow inner plunger configured to slidably receive the first plunger therein in sealing engagement, the hollow inner plunger comprising:
a hollow body including a continuous cylindrical wall defining a first internal chamber for containing a first component, the hollow body having a proximal end and a distal end terminating with a single dispensing orifice through which a first component can be dispensed;
a sealing plug having at least one outwardly protruding circumferential sealing ridge for sealing against an inner wall of a hollow syringe barrel; and
a rupturable membrane attached to the sealing plug and capping and sealing off the single orifice until irreversible rupture of the rupturable membrane by application of sufficient pressure on a first component contained in the first internal chamber so as to irreversibly rupture the rupturable membrane; and
the hollow syringe barrel including an inner wall and a second internal chamber configured to contain therein a second component, the hollow syringe barrel being configured to slidably receive the hollow inner plunger therein in sealing engagement with the at least one circumferential sealing ridge of the sealing plug sealing against the inner wall of the syringe barrel defining the second internal chamber.

28. A syringe-in-syringe mixing system as in claim 27, further comprising:
the first component of a two-component composition initially contained within the first internal chamber of the hollow body of the hollow inner plunger; and
the second component of the two-component composition initially contained within the second internal chamber of the hollow syringe barrel.

\* \* \* \* \*